United States Patent [19]

Calderazzo et al.

[11] Patent Number: 5,210,244

[45] Date of Patent: May 11, 1993

[54] PROCEDURE FOR THE PRODUCTION OF VANADIUM BIS-ARENES FROM VANADIUM OXYCHLORIDE

[75] Inventors: Fausto Calderazzo, Ghezzano; Guido Pampaloni, Pontedera; Francesco Masi, San Donato Milanese; Angelo Moalli, Castelletto Ticino; Maria C. Cassani, Bologna; Renzo Invernizzi, Milan, all of Italy

[73] Assignee: ECP Enichem Polimeri S.r.l., Milan, Italy

[21] Appl. No.: 911,286

[22] Filed: Jul. 9, 1992

[30] Foreign Application Priority Data

Jul. 12, 1991 [IT] Italy .................. MI91 A/001934
Jul. 12, 1991 [IT] Italy .................. MI91 A/001937

[51] Int. Cl.$^5$ .......................... C07F 17/00; C07F 9/00
[52] U.S. Cl. ........................................................ 556/43
[58] Field of Search ............................................ 556/43

[56] References Cited

U.S. PATENT DOCUMENTS

| | | | |
|---|---|---|---|
| 3,068,258 | 12/1962 | Pruett et al. | 260/429 |
| 3,231,593 | 1/1966 | Hafner et al. | 260/429 |
| 4,526,724 | 7/1985 | Pillsbury | 556/43 |
| 4,980,491 | 12/1990 | Calderazzo et al. | 556/43 |
| 4,987,111 | 1/1991 | Calderazzo et al. | 502/113 |

FOREIGN PATENT DOCUMENTS 0398402 11/1990 European Pat. Off. .

OTHER PUBLICATIONS

De Liefde Meijer, H. J. et al., Recueil Des Travaux Chimiques Des Pays Bas, vol. 85, No. 9/10, 1966 (pp. 1007-1017)—Studies In Transition Metal Chemistry, Part IV, The Suitability of Cyclo pentadienylvanadium Compounds As Components of Ziegler-Type Polymerization Catalysts.

*Primary Examiner*—José G. Dees
*Assistant Examiner*—Porfirio Nazario
*Attorney, Agent, or Firm*—George P. Hoare, Jr.

[57] ABSTRACT

A procedure is described for the preparation of a vanadium bis-arene, [V(arene)$_2$], starting from vanadium oxychloride, aluminium metal, aluminium trichloride and an arene, wherein:

(a) vanadium oxychloride (VOCl$_3$), active aluminium metal, and aluminium trichloride are put in contact with each other, in a liquid arene, to transform the vanadium oxychloride into the complex compound [V(arene)$_2$]$^+$ [AlCl$_4$]$^-$;

(b) a liquid cyclic or acyclic or acyclic ether is added to the reaction product of step (a) to reduce [V(arene)$_2$]$^+$ to [V(arene)$_2$]; and (c) the vanadium bis-arene [V(arene)$_2$] is recovered from the reacton product of step (b).

The vanadium bis-arenes thus obtained are use in the preparation of catalysts for the polymerization of olefins.

19 Claims, No Drawings

PROCEDURE FOR THE PRODUCTION OF VANADIUM BIS-ARENES FROM VANADIUM OXYCHLORIDE

DESCRIPTION

The present invention relates to a procedure for the production of vanadium bis-arenes starting from vanadium oxychloride.

Vanadium bis-arenes are compounds which are useful in the art, especially for the preparation of polymerization catalysts of olefins, as described, for example in U.S. Pat. No. 4,987,111.

Various procedures for the preparation of vanadium bis-arenes are already known in the art. For example, E. O. Fischer and H. P. Kogler, in Chem. Berg. 90, 250, 1957, describe the preparation of vanadium bis-benezene [V(C$_6$H$_6$)$_2$] starting from vanadium tetrachloride, aluminium metal, aluminium trichloride and benzene. In addition, F. Calderazzo in Inorg. Chem. 3 810 (1964) describes the preparation of vanadium bis-mesithylene [V(mesithylene)$_2$] starting from vanadium trichloride, aluminium metal, aluminium trichloride and mesithylene. These procedures, however, give very limited yields in the end reaction product and are consequently not highly considered from an industrial point of view.

U.S. Pat. No. 4,980,491 describes a procedure for the production of vanadium bis-arenes which includes the formation of a complex compound [V(arene)$_2$]$^+$[AlCl$_4$]$^-$ by the reaction of vanadium trichloride, aluminium metal and aluminium trichloride, operating in the presence of an arene, the reaction of the complex compound with an alkaline iodide to give a vanadium bis-arene iodide, and the reduction of the later with a metallic or organometallic reducing agent.

In Italian Patent Application 19.111 A/90 filed on Jan. 19, 1990, by the Applicant, a procedure is described for the production of vanadium bis-arenes wherein the complex compound [V(arene)$_2$]$^+$[AlCl$_4$]$^-$ is put in contact with a cyclic or acyclic liquid aliphatic ether to cause the reduction of [V(arene)$_2$]$^+$ into [V(arene)$_2$].

As far as the Applicant is aware of, there are no known procedures for the preparation of vanadium arenes starting from compounds of pentavalent vanadium, in particular vanadium oxychloride. The latter compares advantageously with vanadium chlorides with respect to cost, availability and processability.

It has now been found, according to the present invention, that it is possible to prepare vanadium bis-arenes starting from vanadium oxychloride (VOCl$_3$), active aluminium metal, aluminium trichloride and an arene by means of a procedure with several steps with the progressive reduction of the oxidation state of the vanadium, giving unexpectedly improved yields of the end reaction product. The term active aluminium metal, according to the present invention, refers to an aluminium having a 99% or more purity by weight, at least 90% by weight of which being capable of rapidly developing hydrogen in a basic aqueous environment.

In according with this, the present invention relates to a procedure for the preparation of a vanadium bis-arene [V(arene)$_2$], starting from vanadium oxychloride, aluminium metal, aluminium trichoride and an arene, wherein:

(a) vanadium oxychloride (VOCl$_3$), active aluminium metal and aluminium trichloride are put in contact with each other, in a liquid arene, to transform the vanadium oxychloride into the complex compound [V(arene)$_2$]$^+$[AlCl$_4$]$^-$ (b) a liquid cyclic or acyclic ether is added to the reaction product of step (a) to reduct [V(arene)$_2$]$^+$ to [V(arene)$_2$]; and (c) the vanadium bis-arene [V(arene)$_2$] is recovered from the reaction product of step (b).

Step (a)

In step (a) of the procedure of the present invention, vandium oxychloride, active aluminium metal, aluminium trichloride and an arene are put in contact with each other, under reaction conditions.

As already specified, aluminium metal, active in the procedure of the present invention, is an aluminium having a purity of 99% or more, at least 90% by weight of which is capable of rapidly developing hydrogen in a basic aqueous environment. More specifically, an active aluminium of this kind is capable of developing after 5 minutes, in a basic aqueous environment, a quantity of hydrogen of at least 800 ml, measured at atmospheric pressure and at 25° C., for every gram of aluminium. The impurities present in this kind of aluminium are generally composed of aluminium oxides. An active aluminium is obtained, for example, in metallurgical aluminium rolling procedures. The aluminium used in step (a) of the procedure will conveniently have a particle size which is less than 100 μm, and an apparent desensity of about 0.10 to 0.13 g/ml.

According to a preferred of the present invention, step (a) may be carried out in two consecutive steps (a') and (a''), wherein:

(a') vanadium oxychloride is first trasformed into a vanadium chloride in its oxidation state (III) by contacting it, in a liquid arene, with active aluminium metal and aluminium chloride.

(a'') a further quantity of aluminium metal is added to the reaction mixture of step (a') to form the complex compound [V(arene)$_2$]$^+$[ALCl$_4$]$^-$.

In step (a') it is convenient to operate with a molar ratio between the aluminium trichloride and vanadium oxychloride of 0.33 to 2 and with a molar ratio between the aluminium metal and vanadium oxychloride of 0.7 to 10. The quantity of arene present in step (a') is not vital and may generally vary from 2 to 10 moles for each mole of vanadium oxychloride. It is generally preferable to use an excess of arene, for example from 4 to 10 moles per mole of vanadium oxychloride, the excess having the function of solvent or diluent. The best results are obtained by operating with a molar ratio between the aluminium trichloride and vanadium oxychloride of 1 to 2 and with a molar ratio between the aluminium metal and vanadium oxychloride of 0.7 to 4. Moreover, step (a') is carried out at room temperature (20°–25° C.) or at temperature values close to room temperature (for example from 20° to 50° C.), controlling the exothermal reaction to keep the temperature within the above limits. Under these conditions, a complete, or substantially complete, reduction of the vanadium to its oxidation state (III) is obtained over a period of about 1-2 hours.

In step (a'') of the procedure, the reaction product of step (a'), generally in the form of a suspension, is put in contact with aluminium metal to cause the formation of the complex compound [V(arene)$_2$]$^+$[AlCl$_4$]$^-$.

In particular, in step (a'') it is preferable to operate with a molar ratio between the additional aluminium metal and vanadium of 1 to 2, at a reaction temperature ranging from room temperature to 150° C. and for a period of 2 to 4 hours. Under the preferred conditions, the molar ratio between the additional aluminum metal and vanadium ranges from 1.3 to 1.6, at a temperature of about 120°-130° C. and for a period of 2-3 hours. The aluminium used in step (a″) is preferably an active aluminium, as previously defined, or it may be a non-active aluminium.

In a second embodiment of the present invention, in step (a) of the procedure, vanadium oxychloride, active aluminium metal and aluminium trichloride in excess of the stoichiometric value are put in contact with each other, in a liquid arene and under reaction contidions, the advantage being the elimination, or substantial elimination of disactivating phenomena.

According to this second embodiment, in step (a) of the procedure, vanadium oxychloride (VOCl$_3$), active aluminium metal and aluminium trichloride are put in contact with each other, with a molar ratio between the aluminium trichloride and vanadium oxychloride equal to or higher than 2 and with a molar ratio between the aluminium metal and vanadium oxychloride equal to or higher than 2, in the liquid arene, to form the complex compound [V(arene)$_2$]$^+$[AlCl$_4$]$^-$.

In this second embodiment, the higher limit of the molar ratio between aluminium trichloride and vanadium oxychloride in step (a) is not critical, and may have values as high as 20. However, for economical reasons, this value should be kept at a value of about 2. Similarly the higher limit of the molar ratio between active aluminium metal and vanadium oxychloride is not critical, and may reach values as high as 10. However, for economical reasons, this ratio should be kept within a range of 2 to 3. The reagents may be completely fed at the beginning of the reaction of step (a). Alternatively, the aluminium trichloride may be partly fed at the beginning of the reaction, together with the other reagents, and the remaining part during the reaction.

According to this second embodiment, step (a) is moreover carried out at a temperature ranging from 25° to 170° C. and for a period of 2 to 4 hours and preferably at a temperature of 120°-130° C. and for a period of 2-3 hours.

Specific examples of arenes suitable for being used in step (a) of the present invention, are toluene, p-xylene and mesitylene. Among these mesitylene is preferred. The quantity of arene present in step (a) is not critical and may generally vary from 2 to 10 moles for each mole of vanadium oxychloride. It is generally preferable to use an excess of arene, the excess having the function of solvent or diluent.

Under the conditions above specified for step (a) of the procedure, a generally reddish-brown suspension, of the complex compound [V(arene)$_2$$^+$[AlCl$_4$]$^-$ in the liquid arene, is obtained as reaction product.

Step (b)

In step (b) of the procedure a cyclic or acyclic liquid ether is added to the suspension resulting from step (a) to cause the reduction of [V(arene)$_2$]$^+$ to [V(arene)$_2$].

Ethers suitable for the purpose are tetrahydrofuran, ethyl ether, dimethoxyethane, diethylene glycol dimethylether and their mixtures. Among these tetrahydrofuran and the mixtures of tetrahydrofuran and dimethoxyethane are preferred. The quantity of ether added is not critical; however, quantities of 100 to 200 parts by weight for every 100 parts by weight of the reaction mixture are normally used for the purpose. At this stage of the reaction a diluent may be added to the reaction mixture, preferably a hydrocarbon diluent, liquid under the operating conditions and preferably a saturated aliphatic hydrocarbon, for example heptane. The treatment with ether may be carried out at a temperature ranging from 0° to 50° C., but preferably at room temperature (20°-25° C.) or at values close to those of room temperature. The contact times may generally vary from 2 to 48 hours and will be preferably 2-5 hours.

Operating under these conditions the vanadium arene is obtained in the form of a solution in the solvent mixture used.

Step (c)

In step (c) of the procedure of the present invention, the vanadium arene obtained in step (b) can be separated from the reaction mixture using normal separating techniques. For example the separation can be carried out by evaporating the ether and possible hydrocarbon diluent from the reaction mixture. The distillation residue may be recovered in a solvent capable of dissolving the vanadium arene, such as a hydrocarbon solvent, especially an aliphatic hydrocarbon solvent, such as heptane or cyclohexane. The solution thus obtained can be separated from the solid co-products of the reaction by filtration or centrifugation. The vanadium arene may then be recovered from the solution by evaporating the solvent, or by crystallization by cooling the solution to a low temperature.

The vanadium bis-arenes thus obtained are solid products with a defined melting point in an inert atmosphere. These vanadium bis-arenes may be reacted with titanium tetrachloride to prepare solid catalyst compounds which, together with an aluminium trialkyl, are highly active in the polymerization of ethylene or in the copolymerization of ethylene with a $C_3-C_{10}$ alpha-olefin, in procedures carried out in suspension at low pressure and low temperature, in procedure at high pressure and high temperature carried out in a tubular reactor or vessel and in procedures at a high temperature carried out in solution.

The experimental examples which follow provide a better illustration of the present invention.

EXAMPLE 1.

The following products are charged, in order, into a 250 ml glass flask, equipped with a thermometer, magnetic stirrer and reflux cooler: 0.62 g (23 mmoles) of aluminium metal [plate, with a content of aluminium active for the development of hydrogen of 93% by weight, an apparent density of 0.13 g/ml, and with the following particle size: residue at 74 μm: 4.9%, residue at 44 μm: 19.3% and residue at 100 μm: absent]; 5.5 g (41 mmoles) of aluminium trichloride; and 25.9 g (216 mmoles) of mesitylene. After stirring this suspension for about 30 minutes at 25° C., 6.1 g (35 mmoles) of vanadium oxychloride (VOCl$_3$) with a molar ratio of V:Al:AlCl$_3$ of 1:0.66:1.2 are added thereto. After 1 hour of stirring at 25° C., 1.3 g (48 mmoles) of lamellar aluminium metal are added, having the above characteristics, with a total molar ratio Al:V of 2,1. On heating to 130° C. for 3 hours a dark red-brown suspension is obtained. After cooling to 25° C., 100 ml of a mixture composed of 15 ml of tetrahydrofuran and 85 ml of dimethoxyethane are added. The mixture is kept under vigorous stirring for 3 hours. After filtration, the solution obtained is evaporated until dry (0.1 Torr; 50° C.). The residue is added to 100 ml of anhydrous cyclohexane and a reddish-brown solution is obtained containing 9.7 g (33 mmoles) of vanadium bis-mesitylene [V(mesitylene)$_2$] with a 94% yield with respect to the initial VOCL$_3$.

The following products are charged, in order, into a 250 ml glass flask, equipped with a thermometer, magnetic stirrer and reflux cooler: 0.62 g (23 mmoles) of aluminium metal, having the characteristics described in Example 1; 2.75 g (21 mmoles) of aluminium trichloride; and 16.8 g (140 mmoles) of mesithylene. After about 30 minutes of stirring at 25° C., 6.1 g (35 mmoles) of vanadium oxychloride (VOCL$_3$), with a molar ratio V:Al:AlCl$_3$ equal to 1:0.66:0.6 are added to the suspension. After 1 hour of stirring at 25° C., 1.9 g (70 mmoles) of lamellar aluminium metal, equal to a total molar ratio Al:V of 2.66, are added. On heating to 130° C. for 3 hours a dark reddish-brown suspension is obtained. After cooling to 25° C., 100 ml of a mixture composed of 15 ml of tetrahydrofuran and 85 ml of dimethoxyethane are added. The mixture is kept under vigorous stirring for 3 hours. After filtration, the solution obtained is evaporated until dry (0.1 Torr; 50° C.). The residued is added to 100 ml of anhydrous cyclohexane and a reddish-brown solution is obtained, containing 9.57 g (33 mmoles) of vanadium bis-mesithylene [V(mesithylene)$_2$], with a 94% yield with respect to the initial VOCl$_3$.

EXAMPLE 3

The following products are charged, in order, into a 250 ml glass flask, equipped with a thermometer, magnetic stirrer and reflux cooler: 0.94 g (35 mmoles) of aluminium metal, having the characteristics described in Example 1; 5.5 g (41 mmoles) of aluminium trichloride; and 16.8 g (140 moles) of mesitylene. After about 30 minutes of stirring at 25° C., 6.1 g (35 mmoles) of vanadium oxychloride (VOCl$_3$), with a molar ratio V:Al:AlCl$_3$ of 1:1:1.2, are added to the suspension. After 1 hour of stirring at 25° C. 1.3 g (48 mmoles) of lamellar aluminium metal, with a total molar ratio Al:V of 2,4, are added. On heating to 130° C. for 3 hours, a dark reddish-brown suspension is obtained. After cooling to 25° C., 200 ml of a mixture composed of 30 ml of tetrahydrofuran and 170 ml of dimethoxyethane, are added. After filtration, the solution obtained is evaporated until dry (0.1 Torr; 50° C.). The residue is mixed with 100 ml of anhydrous heptane. After further filtration, the solution is concentrated to 20 ml and cooled to −78° C. Vanadium bis-mesitylene [V(mesitylene)$_2$] (9.2 g; 32 mmoles) is collected in the form of a crystalline product, with a 90% yield with respect to the initial VOCl$_3$.

EXAMPLE 4

The following products are charged, in order, into a 250 ml glass flask equipped with a thermometer, magnetic stirrer and reflux cooler: 0.62 g (23 mmoles) of aluminium metal, having the characteristics described in Example 1; 5.5 g (41 mmoles) of aluminium trichloride; and 21.8 g (236 mmoles) of toluene. After about 30 minutes of stirring at 25° C., 6.1 g (35 mmoles) of vanadium oxychloride (VOCl$_3$), with a molar ratio V:Al:AlCl$_3$ of 1:0.66:1.2, are added to the suspension. After 2 hours of stirring at 120° C., 1.3 g (48 mmoles) of lamellar aluminium metal, with a total molar ratio Al:V of 2,1, are added. On reflux heating for 13 hours a dark reddish-brown suspension is obtained. After cooling to 25° C., 100 ml of a mixture composed of 15 ml of tetrahydrofuran and 85 ml of dimethoxyethane are added. The mixture is kept under vigorous stirring for 3 hours. After filtration, the solution obtained is evaporated until dry (0.1 Torr; 50° C.). The residue is mixed with 100 ml of anhydrous cyclohexane, obtaining a reddish-brown solution containing 5.6 g (24 mmoles) of vanadium bis-toluene [V(toluene)$_2$], with a 68% yield with respect to the initial VOCl$_3$.

EXAMPLE 5

The following products are charged in order into a 250 ml glass flask equipped with a thermometer, magnetic stirrer and reflux cooler: 1.888 g (70 mmoles) of aluminium metal having the characteristics described in example 1; 14 g (105 mmoles) of aluminium trichloride; and 43.2 g (359.4 mmoles) of mesitylene. 6.1 (35 mmoles) of vanadium oxychloride (VOCl$_3$) with a molar ratio V:Al:AlCl$_3$ of 1:2:3, are added to this suspension, after 30 minutes of stirring at 25° C. After heating to 130° C. for 3 hours a dark reddish-brown suspension is obtained. After cooling to 25° C., 50 ml of tetrahydrofuran are added and the mixture is kept under vigorous stirring for 3 hours at room temperature. After filtration, the solution obtained is evaporated to dryness (0.1 Torr; 50° C.). The residue is recovered with 100 ml of anhydrous cyclohexane, a reddish-brown solution is obtained, containing 6.12 g (21 mmoles) of vanadium bis-mesitylene [V(mesitylene)$_2$], with a yield of 60% with respect to the initial VOCl$_3$.

EXAMPLE 6

The following products are charged in order into a 250 ml glass flask equipped with a thermometer, magnetic stirrer and reflux cooler: 1.888 g (70 mmoles) of aluminium metal having the characteristics described in Example 1, 5.6 g (42 mmoles) of aluminium trichloride; and 43.2 g (360 mmoles) of mesitylene. 6.1 g (35 mmoles) of vanadium oxychloride (VOCl$_3$), with a molar ratio V:Al:AlCl$_3$ of 1:2:1.2, are added to this suspension, after 30 minutes of stirring at 25° C. The reaction is hexothermal and after 1 hour of stirring 3.73 g (28 mmmoles) of aluminium trichloride are added. With this addition the molar ratio V:Al:AlCl$_3$ becomes 1:2:2. After heating to 130° C. for 3 hours a dark reddish-brown suspension is obtained. After cooling to 25° C., 50 ml of tetrahydrofuran are added and the mixture is kept under vigorous stirring for 3 hours at room temperature. After filtration, the solution obtained is evaporated to dryness (0.1 Torr; 50° C.). The residue is recovered with 100 ml of anhydrous cyclohexane and a reddish-brown solution is obtained containing 7.43 g (25.5 mmmoles) of vanadium bis-mesitylene [V(mesitylene)$_2$], with a yield of 73.4% with respect to the initial VOCl$_3$.

EXAMPLE 7

The following products are charged in order into a 500 ml glass flask equipped with a thermometer, a magnetic stirrer and reflux cooler: 72.4 g (603 mmoles) of mesitylene, 18.4 (106 mmoles) of VOCl$_3$ and 5.70 g (211 mmoles) of active aluminium metal having the characteristics described in Example 1. 28 g (210 mmoles) of aluminium trichloride, with a molar ratio V:Al:AlCl$_3$ of 1:2:2, are then added, under stirring, at a temperature of 25° C. A vigorous hexothermal reaction takes place. The mixture is kept for 2 hours at 140° C. and a dark reddish-brown suspension is obtained. After cooling to room temperature, 135 ml of tetrahydrofuran are added to this suspension, and the mixture is kept under vigourous stirring for 3 hours at room temperature. It is then evaporated to dryness (0.1 Torr; 50° C.) and the residue is recovered in 150 ml of anhydrous cyclohexane. The solution is filtered and, after washing the solid with tetrahydrofuran, a reddish-brown solution is obtained containing 16 g (55 mmoles) of vanadium bis-mesitylene [V(mesitylene)$_2$], with a yield of 52% with respect to the initial VOCl$_3$.

EXAMPLE 8

The following products are charged in order into a 500 ml glass flask equipped with a thermometer, magnetic stirrer and reflux cooler: 72.4 g (603 mmoles) of mesitylene, 18.4 g (106 mmoles) of VOCl$_3$ and 5.70 g (211 mmoles) of active aluminium metal having the characteristics described in Example 1. 28 (210 mmoles) of aluminium trichloride, with a molar ratio V:Al:AlCl$_3$ of 1:2:2 are then added, under stirring, at a temperature of 25° C. A strong hexothermal reaction takes place. The mixture is kept for 2 hours at 140° C. and a dark reddish-brown suspension is obtained. After cooling 1.70 g (63 mmoles) of aluminium metal having the characteristics described in Example 1 and 135 ml of anhydrous tetrahydrofuran are added in order to the suspension. The suspension is kept under vigorous stirring for 3 hours at room temperature. It is evaporated to dryness (0.1 Torr, 50° C.) and the residue is recovered with anhydrous cyclohexane. It is filtered, and after washing the solid with tetrahydrofuran, 200 ml of a reddish-brown solution containing 21.1 g (72 mmoles) of vanadium bis-mesitylene [V(mesitylene)$_2$] are obtained, with a yield of 68% with respect to the initial VOCl$_3$.

EXAMPLE 9 (comparative)

The following products are charged, in order, into a 250 ml glass flask equipped with a thermometer, magnetic stirrer and reflux cooler: 1.52 g (56 mmoles) of aluminium metal, having the characteristics described in Example 1; 2.5 g (19 mmoles) of aluminium trichloride; and 42.3 g (352 mmoles) of mesitylene. After about 30 minutes of stirring at 25° C., 4.85 g (28 mmoles) of vanadium oxychloride (VOCl$_3$), with a molar ratio V:Al:AlCl$_3$ of 1:2:0.68, are added to the suspension. After 3 hours of stirring at 130° C., a brown suspension is obtained. After cooling to 25° C., 100 ml of a mixture composed of 15 ml of tetrahydrofuran and 85 ml of dimethoxyethane are added. The mixture is kept under vigorous stirring for 15 hours. After filtration, the solution obtained is evaporated until dry (0.1 Torr; 50° C.). The residue is mixed with 100 ml of anhydrous cyclohexane. There is no solubilization. Analysis carried out on the solid shows that 95% vanadium is present in the form of compounds which are not soluble in an organic solvent.

EXAMPLE 10 (comparative)

The following products are charged, in order, into a 500 ml glass flask, equipped with a thermometer, magnetic stirrer and reflux cooler: 4.72 g (175 mmoles) of aluminium metal, having the characteristics described in Example 1; 5.5 g (41 mmoles) of aluminium trichloride; and 42.3 g (352 mmoles) of mesitylene. After about 30 minutes of stirring at 25° C., 6.1 g (35 mmoles) of vanadium oxychloride (VOCl$_3$), with a molar ratio V:Al:AlCl$_3$ of 1:5:1.2, are added to the suspension. After 1 hour of stirring at 25° C., the mixture is heated to 130° C. for 3 hours, obtaining a slightly orange-coloured suspension. After cooling to 25° C., 50 ml of a mixture composed of 10 ml of tetrahydrofuran and 40 ml of dimethoxy ethane are added. The mixture is kept under vigorous stirring for 3 hours. After filtration, the solution obtained is evaporated until dry (0.1 Torr; 50° C.). The residue is mixed with 100 ml of anhydrous cyclohexane. A slightly red-coloured solution is obtained, containing 0.51 g (1.75 mmoles) of vanadium mesitylene [V(mesitylene)$_2$], with a 5% yield with respect to the initial VOCl$_3$.

EXAMPLE 11

The following products are charged, in order, into a 250 ml glass flask, equipped with a thermometer, magnetic stirrer and reflux cooler: 0.62 g (23 mmoles) of aluminium metal obtained by means of the spray-drying technique, with a content of aluminium metal active for developing hydrogen of 75% by weight and with an apparent density of 0.27 g/ml; 5.5 g (41 mmoles) of aluminium trichloride; and 25.9 g (216 mmoles) of mesitylene. After about 30 minutes of stirring at 25° C., 6.1 g (35 mmoles) of vanadium oxychloride (VOCl$_3$), with a molar ratio V:Al:AlCl$_3$ of 1:0.66:1.2, are added to the suspension. After 1 hour of stirring at 25° C., 1.3 g (48 mmoles) of aluminium having the above characteristics, with a total molar ratio Al:V of 2,1, are added. After 3 hours of stirring at 130° C., a dark reddish-brown suspension is obtained. After cooling to 25° C., 100 ml of mixture composed of 15 ml of tetrahydrofuran and 85 ml of dimethoxyethane are added. The mixture is kept under vigorous stirring for 3 hours. After filtration, the solution obtained is evaporated until dry (0.1 Torr; 50° C.). The residue is mixed with 100 ml of anhydrous cyclohexane. A reddish-brown solution is obtained, containing 5.1 g (17.5 mmoles) of vanadium bis-mesitylene [V(mesitylene)$_2$], with a 50% yield with respect to the initial VOCl$_3$.

EXAMPLE 12 (comparative)

The following products are charged, in order, into a 250 ml glass flask, equipped with a thermometer, magnetic stirrer and reflux cooler: 0.62 g (23 mmoles) of aluminum metal taken from 0.1 mm thick aluminium sheets, cut into thin strips 99.5% purity of aluminium by weight); 5.5 g (41 mmoles) of aluminium trichloride; and 25.9 g (216 mmoles) of mesitylene. After about 30 minutes of stirring at 25° C., 6.1 g (35 mmoles) of vanadium oxychloride (VOCl$_3$), with a molar ratio V:Al:AlCl$_3$ of 1:0.66:1.2, are added to the suspension. After 1 hour of stirring at 25° C., 1.3 g (48 mmoles) of aluminium having the above characteristics, with a total molar ratio Al:V of 2,1, are added. After 3 hours of stirring at 130° C., a dark reddish-brown suspension is obtained. After cooling to 25° C., 100 ml of a mixture composed of 15 ml of tetrahydrofuran and 85 ml of dimethoxyethane are added. The mixture is kept under vigorous stirring for 3 hours. After filtration, the solution obtained is evaporated until dry (0.1 Torr; 50° C.). The residue is mixed with 100 ml of anhydrous cyclohexane. A reddish-brown solution is obtained, containing 0.51 g (1.75 mmoles) of vanadium mesitylene [V(mesitylene)$_2$], with a 5% yield with respect to the initial VOCl$_3$.

EXAMPLE 13 (comparative)

The following products are charged in order into a 250 ml glass flask equipped with a thermometer, magnetic stirrer and reflux cooler: 1.888 g (70 mmoles) of active aluminium metal having the characteristics described in Example 1, AlCl$_3$ (5.6 g; 42 mmoles), mesitylene (43 g; 360 mmoles) and VOCl$_3$ (6.1 g; 35 mmoles), with a molar ratio V:Al:AlCl$_3$ equal to 1:2:1.2. A strong hexothermal reaction takes place. After 1 hour of stirring at room temperature, the mixture is heated for 3 hours to 160°-170° C., and a dark reddish-brown suspension is obtained. After cooling to room temperature, 50 ml of a mixture of tetrahydrofuran-dimethoxyethane 18.85 (v/v) are added to this suspension and vigorous stirring is maintained at room temperature for 3 hours. After filtration, the filtrate is dried (0.1 Torr; 50° C.) and the residue is treated with heptane (50 ml). The resulting solution is filtered, concentrated and cooled to −80° C. 3.6 g of vanadium bis-mesitylene are obtained corresponding to a yield of 35%.

We claim:

1. Process for the preparation of a vanadium bis-arene [V(arene)$_2$], starting from vanadium oxychloride, aluminium metal, aluminium trichloride and an arene, said process comprising:
    (a) contacting vanadium oxychloride (VOCl$_3$), active aluminium metal and aluminium trichloride with each other, in a liquid arene, to transform the vanadium oxychloride into the reaction product complex compound [V(arene)$_2$]*[AlCl$_4$]$^-$;
    (b) adding a liquid cyclic or acyclic ether to the reaction product of step (a) to reduce the [V(arene)$_2$]* to [V(arene)$_2$]; and
    (c) recovering the vanadium bis-arene [V(arene)$_2$] from the reaction product of step (b).

2. Process according to claim 1, wherein in step (a), an active aluminium is used, with a particle size less than 100 μm, and an apparent density of 0.10 to 0.13 g/ml and an arene is used selected from the group consisting of toluene, p-xylene and mesitylene, operating with a quantity of arene of 2 to 10 moles per mole of vanadium oxychloride.

3. Process according to claim 1 wherein step (a) is carried out in two consecutive steps, (a') and (a''), wherein steps (a') and (a'') comprise:
    (a') transforming vanadium oxychloride into a vanadium chloride in its oxidation state (III) by contacting it, in the liquid arene, with active aluminium metal and aluminium trichloride, with a molar ratio between the aluminium trichloride and vanadium oxychloride of 0.33 to 2 and with a molar ratio between the aluminium metal and vanadium oxychloride of 0.7 to 10, at or about room temperature (20°-25° C.) for a period of about 1-2 hours;
    (a'') adding a further quantity of aluminium metal to the reaction mixture of step (a') to form the complex compound [V(arene)$_2$]*[AlCl$_4$].

4. Process according to claim 3, wherein in step (a'), the quantity of arene is from 4 to 10 moles for each mole of vanadium oxychloride, with a molar ratio between the aluminium trichloride and vanadium oxychloride of 1 to 2 and with a molar ratio between the aluminium metal and vanadium oxychloride of 0.7 to 4.

5. Process according to claim 3, wherein, step (a'') is carried out with a molar ratio between the additional aluminium metal and vanadium from 1 to 2, at a reaction temperature from room temperature to 150° C., and for a period of 2 to 4 hours.

6. Process according to claim 5, wherein in step (a'') the molar ratio between the additional aluminium metal and vanadium is from 1.3 to 1.6, at a temperature of 120°-130° C., for a period of 2-3 hours.

7. Process according claim 1, wherein, in step (a) vanadium oxychloride (VOCl$_3$), active aluminium metal and aluminium trichloride, are put in contact, in the liquid arene, with a molar ratio between the aluminium trichloride and vanadium oxychloride equal to or higher than 2 and with a molar ratio between the aluminium metal and vanadium oxychloride equal to or higher than 2.

8. Process according to claim 7, wherein, step (a) is carried out with a molar ratio between aluminium trichloride and vanadium oxychloride of 2 to 20, with a molar ratio between the active aluminium metal and vanadium oxychloride of 2 to 10, at a temperature ranging from 25° to 170° C. and for a period of 1 to 4 hours.

9. Process according to claim 1, wherein step (b) further comprises adding an ether, selected from tetrahydrofuran, ethyl ether, dimethoxyethane, diethyleneglycol dimethylether, or one of their mixtures, in quantities of 100 to 200 parts by weight for every 100 parts by weight of the reaction mixture, the operating temperature ranging from 0° to 50° C., with a contact time of 2 to 48 hours.

10. Process according to claim 1, wherein in step (c) the vanadium bis-arene is separated in a solid form.

11. A process according to claim 5 wherein the additional aluminum metal is comprised of active aluminum.

12. A process according to claim 8 wherein the molar ratio between aluminum trichloride and vanadium oxychloride is about 2.

13. A process according to claim 8, wherein the molar ratio between the active aluminum metal and vanadium oxychloride is from about 2 to 3.

14. A process according to claim 8, wherein the temperature is between about 120°-130° C.

15. A process according to claim 8, wherein the process is carried out for a period of about 2-3 hours.

16. A process according to claim 9, wherein the ether is added in conjunction with a hydrocarbon diluent.

17. A process according to claim 9, wherein the operating temperature is at or about room temperature (20°-25° C.).

18. A process according to claim 9, wherein the contact time is about 2-5 hours.

19. A process according to claim 1, wherein the step (c) the vanadium bis-arene is separated in the form of a solution in an organic solvent.

* * * * *